United States Patent
Choi et al.

(10) Patent No.: US 12,133,873 B2
(45) Date of Patent: Nov. 5, 2024

(54) COMPOSITION FOR PREVENTING, ALLEVIATING, OR TREATING OBESITY OR FATTY LIVER DISEASE, COMPRISING LEUCONOSTOC CITREUM WIKIM0104

(71) Applicant: KOREA FOOD RESEARCH INSTITUTE, Jeollabuk-Do (KR)

(72) Inventors: Hak-Jong Choi, Seo-gu (KR); Seul-Ki Lim, Seo-gu (KR)

(73) Assignee: KOREA FOOD RESEARCH INSTITUTE, Wanju-Gun (KR)

( * ) Notice: Subject to any disclaimer, the term of this patent is extended or adjusted under 35 U.S.C. 154(b) by 593 days.

(21) Appl. No.: 17/433,427

(22) PCT Filed: Feb. 27, 2020

(86) PCT No.: PCT/KR2020/002845
§ 371 (c)(1),
(2) Date: Aug. 24, 2021

(87) PCT Pub. No.: WO2020/175940
PCT Pub. Date: Sep. 3, 2020

(65) Prior Publication Data
US 2022/0047652 A1 Feb. 17, 2022

(30) Foreign Application Priority Data
Feb. 28, 2019 (KR) .................. 10-2019-0024254

(51) Int. Cl.
*A61K 35/744* (2015.01)
*A23L 29/00* (2016.01)
*A61P 1/16* (2006.01)

(52) U.S. Cl.
CPC .......... *A61K 35/744* (2013.01); *A23L 29/065* (2016.08); *A61P 1/16* (2018.01)

(58) Field of Classification Search
CPC ....... A61K 35/744; A23L 29/065; A61P 1/16; A23K 10/16; A23V 2200/30; A23V 2400/11; A23V 2200/332
See application file for complete search history.

(56) References Cited

U.S. PATENT DOCUMENTS

2013/0089633 A1  4/2013  Nakamura et al.

FOREIGN PATENT DOCUMENTS

| | | |
|---|---|---|
| CN | 103037878 A | 4/2013 |
| KR | 10-0872911 B1 | 12/2008 |
| KR | 10-2010-0037310 A | 4/2010 |
| KR | 10-2015-0143252 A | 12/2015 |
| KR | 10-2016-0108645 A | 9/2016 |
| KR | 10-2017-0000510 A | 1/2017 |
| KR | 10-1838280 B1 | 3/2018 |
| KR | 10-1873193 B1 | 7/2018 |
| KR | 10-1937365 B1 | 1/2019 |
| KR | 10-2032982 B1 | 10/2019 |

OTHER PUBLICATIONS

Extended European Search Report dated Jan. 18, 2023 in European Application No. 20763924.6.
Zhang, J., et al., "Effect of *Bifidobacterium longum, Leuconostoc mesenteroides* and *Lactobacillus rhamnosus* on serum superoxide dismutase, glutathione peroxidase, malondialdehyde and liver steatosis of mice", Journal of Xinxiang Medical University, vol. 31, No. 10, Oct. 2014, pp. 786-791.
International Search Report for PCT/KR2020/002845 dated Jun. 17, 2020 [PCT/ISA210].

*Primary Examiner* — Kade Ariani
(74) *Attorney, Agent, or Firm* — Sughrue Mion, PLLC (57) ABSTRACT

The present invention relates to novel *Leuconostoc citreum* WiKim0104 isolated from Kimchi and a composition comprising the same or its use. The present invention provides a method for prevention, improvement and treatment of inflammation, obesity or fatty liver disease of a subject by administering the novel *Leuconostoc citreum* WiKim0104 isolated from Kimchi or a composition comprising thereof. The *Leuconostoc citreum* WiKim0104 according to the present invention shows an inhibitory effect for fatty liver production by inhibiting fat accumulation in liver cells and reducing expression of fatty liver-related genes, and thus it may be variously utilized for uses in prevention, improvement and treatment of inflammation, obesity or fatty liver disease.

3 Claims, 4 Drawing Sheets
Specification includes a Sequence Listing.

```
<400>  1
gatgaacgct ggcggcgtgc ctaatacatg caagtcgaac gcgcagcgag aggtgcttgc     60
acctttcaag cgagtggcga acgggtgagt aacacgtgga taacctgcct caaggctggg    120
gataacattt ggaaacagat gctaataccg aataaaactt agtatcgcat gatatcaagt    180 taaaggcgc tacggcgtca cctagagatg gatccgcggt gcattagtta gttggtgggg     240
taaaggctta ccaagacgat gatgcatagc cgagttgaga gactgatcgg ccacattggg    300
actgagacac ggcccaaact cctacgggag gctgcagtag ggaatcttcc acaatgggcg    360
caagcctgat ggagcaacgc cgcgtgtgtg atgaaggctt tcgggtcgta aagcactgtt    420
gtatgggaag aaatgctaaa atagggaatg attttagttt gacggtacca taccagaaag    480
ggacggctaa atacgtgcca gcagccgcgg taatacgtat gtcccgagcg ttatccggat    540
ttattgggcg taaagcgagc gcagacggtt gattaagtct gatgtgaaag cccggagctc    600
aactccggaa tggcattgga aactggttaa cttgagtgtt gtagaggtaa gtggaactcc    660
atgtgtagcg gtggaatgcg tagatatatg gaagaacacc agtggcgaag gcggcttact    720
ggacaacaac tgacgttgag gctcgaaagt gtgggtagca aacaggatta gataccctgg    780
tagtccacac cgtaaacgat gaatactagg tgttaggagg tttccgcctc ttagtgccga    840
agctaacgca ttaagtattc cgcctgggga gtacgaccgc aaggttgaaa ctcaaaggaa    900
ttgacgggga cccgcacaag cggtggagca tgtggtttaa ttcgaagcaa cgcgaagaac    960
cttaccaggt cttgacatcc tttgaagctt tagagatag aagtgttctc ttcggagaca    1020
aagtgacagg tggtgcatgg tcgtcgtcag ctcgtgtcgt gagatgttgg gttaagtccc    1080
gcaacgagcg caacccttat tgttagttgc cagcattcag ttgggcactc tagcgagact    1140
gccggtgaca aaccggagga aggcggggac gacgtcagat catcatgccc cttatgacct    1200
gggctacaca cgtgctacaa tggcgtatac aacgagttgc caacctgcga aggtgagcta    1260
atctcttaaa gtacgtctca gttcggactg cagtctgcaa ctcgactgca cgaagtcgga    1320
atcgctagta atcgcggatc agcacgccgc ggtgaatacg ttcccgggtc ttgtacacac    1380
cgcccgtcac accatgggag tttgtaatgc ccaaagccgg tggcctaacc              1430
```

COMPOSITION FOR PREVENTING, ALLEVIATING, OR TREATING OBESITY OR FATTY LIVER DISEASE, COMPRISING LEUCONOSTOC CITREUM WIKIM0104

CROSS-REFERENCE TO RELATED APPLICATIONS

This application is a National Stage of International Application No. PCT/KR2020/002845 filed Feb. 27, 2020, which claims priority to Korean Patent Application No. 10-2019-0024254 filed Feb. 28, 2019, the entire disclosures of which are incorporated herein by reference.

TECHNICAL FIELD

The present invention relates to a novel strain isolated from Kimchi and a composition for preventing, improving or treating inflammation, obesity or fatty liver disease comprising the same.

BACKGROUND ART

Fatty liver is a disease in which normal fat metabolism is not achieved due to excessive intake of fat, increase in accumulation and synthesis in the liver, and decrease in excretion, resulting in accumulation of triglycerides in hepatocytes, and when fat accounts for more than 5% of the total liver weight, it is classified as fatty liver.

In addition, due to the recent westernized high-fat, high-calorie westernized diet and lack of exercise because of the development of civilization, the number of fatty liver patients is increasing rapidly, and the age is also increasing from teenagers to after 60 s. When fat is continuously accumulated in the liver, it progresses to fatty hepatitis accompanied by inflammation, and liver cirrhosis may occur due to liver tissue necrosis and fibrosis of the liver because of chronic inflammation. When symptoms worsen further, there is a possibility of developing liver cancer. Therefore, fatty liver is the biggest cause of hepatitis, cirrhosis and liver cancer.

Drugs currently in use on the market include Xenical™ (Roche) which has orlistat as a main ingredient, and Reductil™ (Abbott) which has sibutramine as a main ingredient, and the like, but show side effects such as diarrhea, abdominal pain, and insomnia, and the like, and as a therapeutic agent of fatty liver, fibrate-based drugs represented by clofibrate, and the like are used in clinical practice, but side effects such as liver dysfunction have been reported.

On the other hand, although various lactic acid bacteria in the following Patent document 1 show the effect of improving fatty liver, there is an urgent need to develop a therapeutic agent for fatty liver which has a fundamental effect of preventing or improving fatty liver and does not exhibit the aforementioned side effects.

Meanwhile, Patent document 1 discloses the effect of improving fatty liver of various lactic acid bacteria such as *Bifidobacterium* sp. and *Lactobacillus* sp. and the like, but a therapeutic agent hat has a fundamental therapeutic effect on fatty liver and does not exhibit the aforementioned side effects has not yet been developed. Therefore, there is an urgent need to develop a therapeutic agent that can fundamentally treat fatty liver and has no side effects.

(Patent document 1) KR Patent Application No. 10-1937365 (2018 Aug. 8.)

DISCLOSURE

Technical Problem

The present invention is to provide a novel *Leuconostoc citreum* sp. lactic acid bacterium with excellent efficacy for prevention or improvement of fatty liver disease.

Technical Solution

Accordingly, as the result that the present inventors have tried to find a lactic acid bacteria strain which shows an effect for prevention or improvement of fatty liver from traditional fermented foods, they have isolated and identified a novel Weissella sp. lactic acid bacteria strain, *Leuconostoc citreum* WiKim0104, thereby completing the present invention.

One embodiment of the present invention provides a composition for preventing or improving inflammation, obesity or fatty liver disease comprising *Leuconostoc citreum* WiKim0104, its culture, its lysate or its extract as an active ingredient.

The fatty liver disease may be any one or more selected from the group consisting of simple fatty liver, non-alcoholic steatohepatitis, liver fibrosis and liver cirrhosis.

The composition may be a food composition, a lactic acid bacteria starter composition for food fermentation, a feed or feed additive composition, or a pharmaceutical composition.

The food composition may comprise a health functional food, beverage, bar or fermented oil.

Another embodiment of the present invention provides a use for preventing, improving or treating inflammation, obesity or fatty liver disease of *Leuconostoc citreum* WiKim0104, its culture, its lysate or its extract.

The fatty liver disease may be any one or more selected from the group consisting of simple fatty liver, non-alcoholic steatohepatitis, liver fibrosis and liver cirrhosis.

It may be used as a food composition, a lactic acid bacteria starter composition for food fermentation, a feed or feed additive composition, or a pharmaceutical composition.

One embodiment of the present invention provides a method for preventing, improving or treating inflammation, obesity or fatty liver disease, comprising administering a composition comprising *Leuconostoc citreum* WiKim 0104, its culture, its lysate or its extract to a subject in need thereof. The subject may be an animal including a human.

A method for preventing, improving or treating inflammation, obesity or fatty liver disease, in which the fatty liver disease comprises any one or more selected from the group consisting of simple fatty liver, non-alcoholic steatohepatitis, liver fibrosis and liver cirrhosis is provided.

The present invention provides *Leuconostoc citreum* WiKim0104.

The *Leuconostoc citreum* WiKim0104 of the present invention is a *Leuconostoc citreum* novel strain derived from Kimchi. Although *Leuconostoc citreum* WiKim0104 is isolated and identified from Kimchi in the present invention, but the means of acquisition is not limited thereto.

The lactic acid bacteria strain isolated by examples in the present invention was shown to have the nucleic acid sequence of SEQ ID NO: 1, as the result of 16S rDNA sequencing for identification and classification of microorganisms.

Thus, the microorganism of the present invention which has the 16S rDNA sequence of SEQ ID NO: 1 was named *Leuconostoc citreum* WiKim0104, and was deposited to Korean Culture Center of Microorganisms on Dec. 14, 2018 (accession number KCCM12420P).

The *Leuconostoc citreum* WiKim0104 of the present invention is a gram-positive bacterium and a facultative anaerobe which can grow under both the aerobic and anaerobic conditions, and it does not form spores, has no motility and cells are in the form of bacilli.

In the following examples, it was confirmed that the *Leuconostoc citreum* WiKim0104 of the present invention inhibited expression of FAS (fatty acid synthase), SCD (lipogenic-related gene), COX-2 (cyclooxygenase-2) and NF-K (inflammatory related gene). This confirmed that the *Leuconostoc citreum* WiKim0104 strain could prevent or improve fatty liver by inhibiting fatty liver production by about 30 to 35%. Therefore, the *Leuconostoc citreum* WiKim0104 according to the present invention may be variously utilized for uses in prevention, treatment or improvement of fatty liver disease of a human or animal.

In addition, as could be confirmed in the following examples, the composition comprising the *Leuconostoc citreum* WiKim0104 as an active ingredient was confirmed to inhibit fat accumulation in hepatocytes (HepG2 cells) and inflammation and improve the efficacy of body weight reduction and blood liver function values and reduce expression of factor genes related to fat metabolism, inflammation and liver fibrosis in the liver tissue. Therefore, the composition may be used as an active ingredient of the composition for prevention, treatment or improvement of inflammation, obesity or fatty liver disease which is one or more selected from the group consisting of simple fatty liver, non-alcoholic steatohepatitis, liver fibrosis and liver cirrhosis.

The present invention provides a composition for prevention, improvement or treatment of inflammation, obesity or fatty liver disease comprising *Leuconostoc citreum* WiKim0104, its culture, its lysate or its extract as an active ingredient.

The *Leuconostoc citreum* WiKim0104 comprised in the composition according to the present invention may be present as a living cell or dead cell, and it may be also present in a dried or freeze-dried form. The form and formulation method of lactic acid bacteria suitable to be comprised in various compositions are well known to those skilled in the art. For example, *Leuconostoc citreum* WiKim0104 may be formulated in the form of a culture obtained by culturing in a known liquid medium or solid medium, or a fermented product obtained by culturing the strain and an additional component together, or an extract obtained by extracting the strain with an organic solvent, or a dissolved substance (or lysate) obtained by dissolving the cell membrane of the strain or crushing or treating homogenization, or the like, but not limited thereto.

In one specific example, the composition may be a composition comprising the *Leuconostoc citreum* WiKim0104 strain present as a living cell or dead cell.

In the present invention, the fatty liver disease may include simple fatty liver, non-alcoholic steatohepatitis, liver fibrosis and liver cirrhosis.

In the present invention, the fatty liver disease may include both alcoholic fatty liver and non-alcoholic fatty liver, and for example, may be non-alcoholic fatty liver induced by high-fat diet. The non-alcoholic fatty liver disease (NAFLD) may include both primary and secondary non-alcoholic fatty liver, and for example, it may be non-alcoholic fatty liver occurred from primary hyperlipidemia, diabetes or obesity.

In one specific example, the composition may be a pharmaceutical composition for preventing or treating inflammation, obesity or fatty liver disease comprising a culture, lysate, fermented product or extract of the *Leuconostoc citreum* WiKim0104 strain.

When the composition according to the present invention is used as a pharmaceutical composition, the pharmaceutical composition of the present invention may be prepared by using a pharmaceutically suitable and physiologically acceptable adjuvant, and as the adjuvant, an excipient, disintegrating agent, sweetener, binding agent, coating material, inflating agent, lubricant, glydent or flavoring agent, or the like.

The pharmaceutical composition may be preferably formulated for administration, as a pharmaceutical composition by further comprising one or more pharmaceutically acceptable carriers in addition to the active ingredient described above.

For example, for formulation to a form of a tablet or capsule, the active ingredient may be combined with an oral and non-toxic pharmaceutically acceptable inactive carrier such as ethanol, glycerol, water, and the like. In addition, when desired or needed, an appropriate binding agent, a lubricant, a disintegrating agent and a coloring agent may also be comprised as a mixture. The appropriate binding agent is not limited thereto, but includes natural sugars such as starch, gelatin, glucose or beta-lactose, natural and synthetic gum such as corn sweetener, acacia, tragacanth or sodium oleate, sodium stearate, magnesium stearate, sodium benzoate, sodium acetate, sodium chloride, and the like. The disintegrating agent is not limited thereto, but includes starch, methyl cellulose, agar, bentonite, xanthan gum, and the like. In the composition to be prepared as a liquid solution, as an acceptable pharmaceutical carrier, which is suitable for sterile and biocompatible ones, saline solution, sterile water, Ringer's solution, buffer saline solution, albumin injection solution, dextrose solution, maltodextrin solution, glycerol, ethanol and one or more mixed components thereof may be used, and if needed, other common additives such as an antioxidant, buffer solution, bacteriostatic agent, and the like may be added. In addition, it may be formulated as an injection formulation such as an aqueous solution, suspension, emulsion and the like, pill, capsule, granule or tablet, by additionally adding a diluent, a dispersing agent, a surfactant, a binding agent and a lubricant.

Moreover, by an appropriate method of the corresponding field, by using the method described in Remington's Pharmaceutical Science, Mack Publishing Company, Easton PA, it may be preferably formulated according to each disease or component.

In one specific example, the present invention provides a food composition for preventing or improving inflammation, obesity or fatty liver disease comprising *Leuconostoc citreum* WiKim0104, its culture, its lysate, its fermented product or its extract as an active ingredient. The food composition may include a form of health functional food or beverage, bar or the like.

In the present invention, the food composition comprising the strain as an active ingredient may comprise a beverage such as fermented oil, and the like. Accordingly, the present invention provides a lactic acid bacteria starter for fermentation consisting of *Leuconostoc citreum* WiKim0104 or its culture.

The food composition according to the present invention may be used as a functional food or added to various kinds of foods as formulated in the same method as the pharmaceutical composition. The food in which the composition of the present invention is added includes for example, beverages, vitamin complexes, health supplement foods, and the like.

The food composition of the present invention may comprise a component commonly added in food preparation, and for example, it includes protein, carbohydrate, fat, nutrients, seasonings, and flavoring agents. The example of the carbohydrate described above is a common sugar such as monosaccharides, for example, glucose, fructose, etc.; disaccharides, for example, maltose, sucrose, oligosaccharide, etc.; and polysaccharides, for example, dextrin, cyclodextrin, etc., and sugar alcohol such as xylitol, sorbitol, erythritol, and the like. As the flavoring agent, a natural flavoring agent [thaumatin, stevia extract (for example, rebaudioside A, glycyrrhizin, etc.)] and a synthetic flavoring agent (saccharin, aspartame, etc.) may be used. For example, when the food composition of the present invention is prepared as drinks and beverages, it may further comprise citric acid, liquid fructose, sugar, glucose, acetic acid, malic acid, fruit juice and various kinds of plant extracts, and the like.

The composition according to the present invention may be used as a feed additive or feed.

When used as a feed additive, the composition may be prepared as a 20 to 90% high concentrate or in a powder or granule form. The feed additive may further comprise any one or one or more of organic acids such as citric acid, fumaric acid, adipic acid, lactic acid, malic acid, etc., or phosphates such as sodium phosphate, potassium phosphate, acidic pyrophosphate, polyphosphate, etc., or natural antioxidants such as polyphenol, catechin, alpha-tocopherol, rosemary extract, vitamin C, green tea extract, licorice extract, chitosan, tannic acid, phytic acid, etc. When used as a feed, the composition may be formulated as a common feed form, and may comprise a common feed component together.

The feed additive and feed may further comprise grains, for example, ground or crushed wheat, oats, barley, corn and rice; plant protein feeds, for example, feeds having rape, bean and sunflower as a main component; animal protein feeds, for example, blood meal, meat meal, bone meal and fish meal; sugars and milk products, for example, dried components consisting of various kinds of powdered milk and whey powder, and the like, and in addition, may further comprise a nutritional supplement, a digestion and absorption enhancer, a growth promoter, and the like.

The feed additive may be administered alone or administered by combining with other feed additives among edible carriers to an animal. In addition, the feed additive may be easily administered to an animal as topdressing or by directly mixing it to animal feed or as an oral formulation separate from feed. When the feed additive is administered separately to animal feed, by combining with a pharmaceutically acceptable edible carrier well known in the corresponding art, it may be prepared as an immediate release or sustained release formulation. This edible carrier may be solid or liquid, for example, corn starch, lactose, sucrose, bean flake, peanut oil, olive oil, sesame oil and propylene glycol. When a solid carrier is used, the feed additive may be a tablet, capsule, powder, troche or lozenge or topdressing in a fine dispersible form. When a liquid carrier is used, the feed additive may be a formulation of gelatin soft capsule, or syrup or suspension, emulsion or solution.

Furthermore, the feed additive and feed may contain an adjuvant, for example, a preservative, stabilizing agent, wetting agent or emulsifier, solution promoter, or the like. The feed additive may be used by immersing, spraying or mixing to add it to animal feed.

The feed or feed additive of the present invention may be applied to numerous animal diets including mammals, poultry and fish.

In the present invention, the animal includes mammals, and it may be used to as mammals, not only a pig, a cow, sheep, a goat, an experimental rodent, and in addition to the experimental rodent, a pet animal (e.g.: dog, cat) and the like, and it may be used to as poultry, a chicken, a turkey, a duck, a goose, a pheasant and a quail, and the like, and it may be used to as fish, a trout, and the like, but not limited thereto.

The amount of the *Leuconostoc citreum* WiKim0104 strain comprised in the composition according to the present invention may be about $10^6$ to $10^{12}$ cfu/g based on 1 time, and for example, it may be $10^7$ to $10^{11}$ cfu/g, $10^8$ to $10^{10}$ cfu/g. When the strain is administered, it is preferable to administer it as a living cell, and before intake, it may be administered as a dead or attenuated form. In addition, when prepared by using culture supernatant, and the like, a sterilization process through a heat treatment process may be additionally performed. The strain amount and daily intake level required to have the minimum effect may vary depending on the body or health condition of a taker, but it may be generally about $10^6$ to $10^{12}$ cfu/g, for example, $10^7$ to $10^{11}$ cfu/g, $10^8$ to $10^{10}$ cfu/g.

Other embodiment of the present invention may be provided as a use for prevention, treatment or improvement of inflammation, obesity or fatty liver disease of a human or animal of *Leuconostoc citreum* WiKim0104.

Other embodiment of the present invention provides a use for prevention, improvement or treatment of inflammation, obesity or fatty liver disease of *Leuconostoc citreum* WiKim0104, its culture, its lysate or its extract.

Other embodiment of the present invention provides *Leuconostoc citreum* WiKim0104, its culture, its lysate or its extract for prevention, improvement or treatment of inflammation, obesity or fatty liver disease.

One embodiment of the present invention provides a method for preventing, improving or treating inflammation, obesity or fatty liver disease, comprising administering a composition comprising *Leuconostoc citreum* WiKim0104, its culture, its lysate or its extract to a subject in need thereof. The subject is an animal including a human, and the example of the animal may be included in the scope of the present invention as long as the aforementioned animals that ingest feed. The fatty liver disease may comprise any one or more selected from the group consisting of simple fatty liver, non-alcoholic steatohepatitis, liver fibrosis and liver cirrhosis.

Advantages and features of the present invention, and methods for achieving them will become apparent with reference to examples described in detail below. However, the present invention is not limited to the examples disclosed below, but will be implemented in a variety of different forms, and is provided only to make the disclosure of the present invention complete, and to completely inform those skilled in the art to which the present invention belongs, the scope of the invention, and the present invention is only defined by the scope of claims.

Advantageous Effects

The *Leuconostoc citreum* WiKim0104 according to the present invention is a lactic acid bacterium isolated from Kimchi, and shows an inhibitory effect on fatty liver production through inhibition of intracellular fat accumulation and reduction of expression of fatty liver-related genes, and therefore, it may be variously used for uses in prevention, improvement and treatment of inflammation, obesity or fatty liver disease. Furthermore, it may be usefully used as a starter for fermentation.

MODE FOR INVENTION

Hereinafter, the present invention will be described in detail by examples. The following examples are intended to illustrate the present invention only, but the scope of the present invention is not limited by the following examples.

Example 1: Identification of *Leuconostoc citreum* WiKim0104

A bacterial single colony obtained by applying an undiluted solution of Kimchi extract on an MRS medium was collected with a loop and cultured in an MRS broth. DNA extraction was performed by using QIAamp DNA Mini Kit (QIAgen, Germany). The extracted DNA was confirmed by using 1% agarose gel, and to amplify a 16S rDNA gene, Polymerase Chain Reaction (PCR) was processed by using extracted genomic DNA as a template, and 30 cycles were performed under PCR conditions of denaturation at 95° C. for 1 minute, annealing at 45° C. for 1 minute and extension at 72° C. for 1 minute and 30 seconds. For the obtained PCR products, the sequence was analyzed by requesting to Macrogen (Seoul, Korea). Identification of bacteria was performed by inductive analysis of Basic Local Alignment Search Tool (BLAST) search engine of National Center for Biotechnology Information (NCBI, www.ncbi.nlm.nih.gov) for 16S rDNA sequence.

The strain isolated by the example of the present invention was shown to have the nucleic acid sequence of SEQ ID NO: 1, as the result of 16S rDNA sequence analysis for identification of microorganisms.

Accordingly, the microorganism of the present invention was named *Leuconostoc citreum* WiKim0104, and deposited to Korean Culture Center of Microorganisms on Dec. 14, 2018 (KCCM12420P).

Example 2: Confirmation of Inhibitory Efficacy of Fat Accumulation and Inflammation in Hepatocytes (HepG2 Cells) of *Leuconostoc citreum* WiKim0104

An in vitro experimental method was devised using a transwell to mimic a human body gut-liver axis.

The *Leuconostoc citreum* WiKim0104 lactic acid bacterium was cultured in an MRS medium at 30° C. for 24 hours. At the end of the culture, to recover microbial cells, it was prepared by performing centrifugation at 6,000 rpm for 5 minutes and rinsing with PBS to remove all remaining medium components.

To culture enterocytes (HT-29 cells) and hepatocytes (HepG2 cells), RPMI-1640 medium in which penicillin/streptomycin and 10% fetal bovine serum were added was used, and co-culture was prepared by using a 6-well plate transwell. Before co-culture, enterocytes were aliquoted in a transwell membrane, and hepatocytes were aliquoted in the 6-well plate, and they were prepared by culturing under the conditions of 37° C., 5% $CO_2$, respectively.

Figure 1:
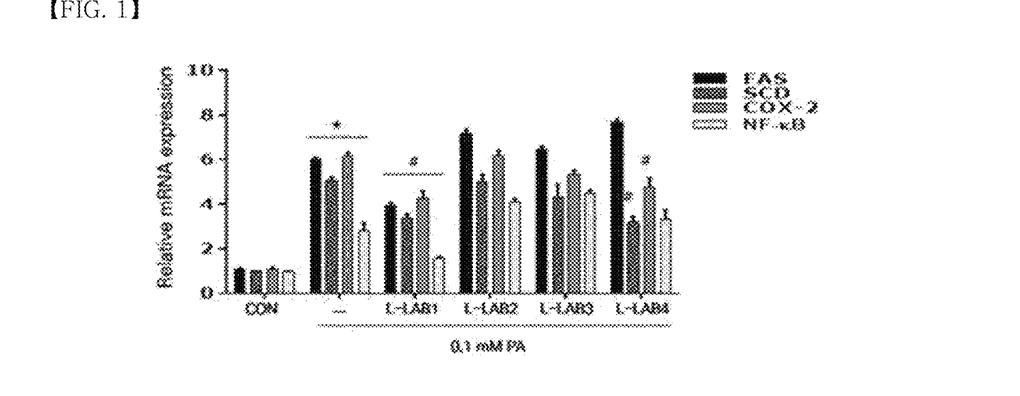
FIG. 1 is a graph of measuring the expression level in HepG2 cells according to treatment of the WiKim0104 strain according to the present invention. L-LAB1 represents *Leu. citreum* WiKim0104, and L-LAB2 represents *Leu. Mesenteroides*, and L-LAB3 and L-LAB4 represent *Leu. citreum* stain #2, #3 isolated in the laboratory, respectively.

When the enterocytes (HT-29 cells) and hepatocytes (HepG2 cells) grew about 80% in a culture dish, the culture solution was replaced with an FBS free medium and they were cultured for 16 hours. After culturing, prepared lactic acid bacteria $1\times10^7$ CFU were treated to the enterocytes, and co-culture of lactic acid bacteria and enterocytes and hepatocytes was performed by assembling a transwell, and fat production in hepatocytes was induced by treating 0.1 mM palmitic acid for 48 hours. After culturing with 0.1 mM palmitic acid for 48 hours, to find out the expression level of fat metabolism and inflammation-related genes in hepatocytes according to the treatment of the *Leuconostoc citreum* WiKim0104, quantitative real time polymerase chain reaction (qPCR) was conducted. As a result, as shown in FIG. 1, it could be confirmed that the gene expression of fatty acid synthase (FAS), and unsaturated fatty acid biosynthesis enzyme (Stearoyl-CoA desaturase, SCD), and inflammation-related factors, COX-2 (Cyclooxygenase-2) and NF-κB (Nuclear factor-kappa B) was significantly reduced, in the hepatocytes (HepG2 cells) in which 0.1 mM palmitic acid and *Leuconostoc citreum* WiKim0104 were co-cultured than the hepatocytes (control) in which 0.1 mM palmitic acid was treated.

Example 3: Confirmation of Body Weight Reduction Efficacy and Improvement of Liver Function Values in Blood Five-week-old male mice (C57BL/6J) were adapted by chow diet (CD; Purina, Korea) in the breeding room environment under the conditions of temperature 20±2° C., humidity 50±5% and light-dark cycle 12 hours unit for 1 week. The experimental animals were fed a normal diet (D12450B, Research Diets, New Brunswick, NJ) or high-fat diet (D12451, Research Diets, New Brunswick, NJ) in which 45% of total calories were fat, and were adapted to the diet for 1 week, and then the experiment was performed. The experimental groups consisted of 3 groups in total, which were the normal diet intake group (ND), high-fat diet intake group (HFD), and intake group receiving daily oral administration of *Leuconostoc citreum* WiKim0104 at a concentration of $2\times10^9$ CFU/200 μl with the high-fat diet (HFD+L-LAB1), and fatty liver was induced through diet for 20 weeks. The normal diet intake group (ND) and high-fat diet intake group (HFD) were orally administered with the same amount of phosphate buffered saline (PBS) daily. In 20 weeks after performing the experiment, the body weight of each experimental group was measured. In addition, to measure the liver function values (serum GOT, serum GPT) in blood of the experimental groups, they were fasted 16 hours before the end of the experiment, and blood was collected from the abdominal vena cava, and serum was separated and used in the experiment.

Figure 2A:
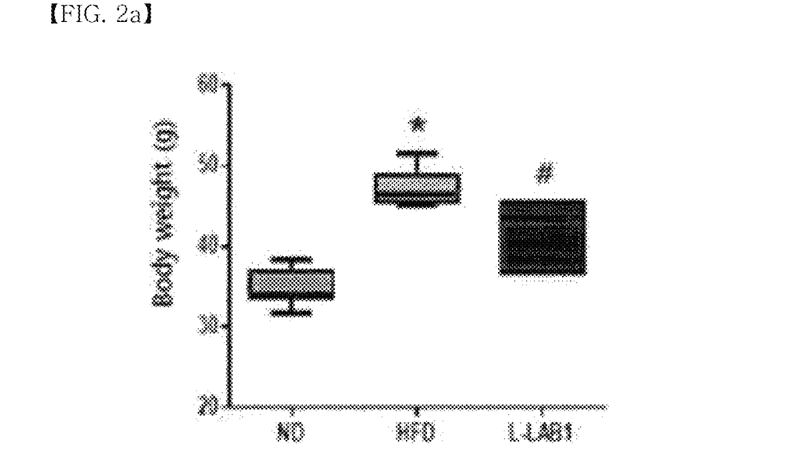
FIGS. 2a to 2c are graphs showing the body weight and liver function values (GPT, GOT) in blood of the fatty liver mouse model according to the intake of the WiKim0104 strain according to the present invention. *P<0.05, compare to the ND; #P<0.05, compare to the HFD. L-LAB1 represents *Leu. citreum* WiKim0104.
Figure 2B:
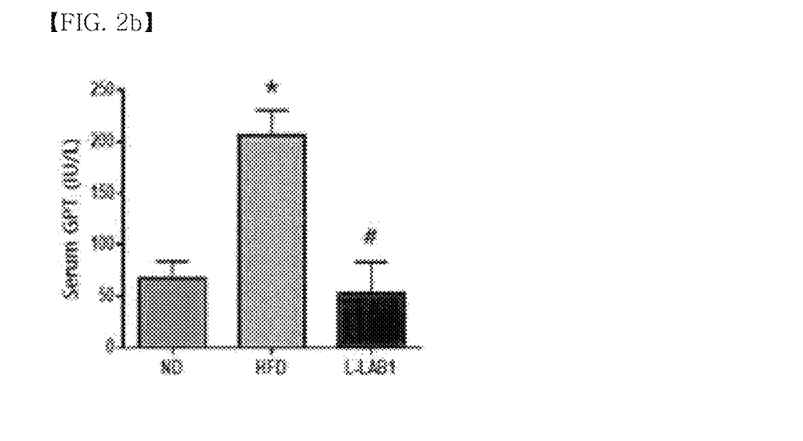
Figure 2C:
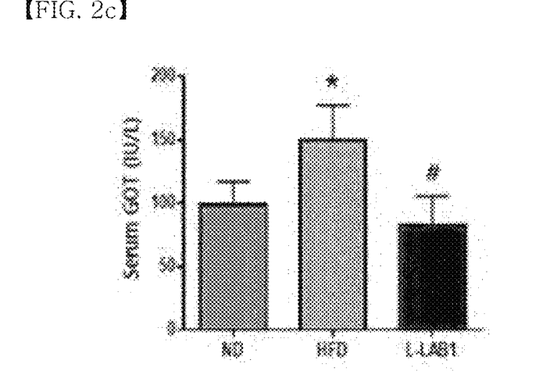

The GOT and GPT in blood were measured by using an automatic biochemical measuring device (FUJI DRI-CHEM 7000i, Fujifilm, Tokyo, Japan), and in FIG. 2a to FIG. 2c, GLUTAMATE-OXALOACETATE TRANSAMINASE (GOT) and GLUTAMATE-PYRUVATE TRANSAMINASE (GPT) in blood were shown as graphs.

As a result, as shown in FIG. 2a to FIG. 2c, it could be confirmed that the body weight and liver function values in blood were significantly reduced when the high-fat diet and *Leuconostoc citreum* WiKim0104 were ingested together (HFD+L-LAB1), compared to the high-fat diet intake mice (HFD).

Example 4: Confirmation of Expression Level of Fat Metabolism, Inflammation and Liver Fibrosis-Related Genes in Liver Tissue To find out the expression level of fat metabolism, inflammation and liver fibrosis-related genes in the liver tissue according to the intake of the *Leuconostoc citreum* WiKim0104 strain, using the liver tissue extracted after the end of experiment, qPCR (quantitative real time polymerase chain reaction) was conducted.

Figure 3A:
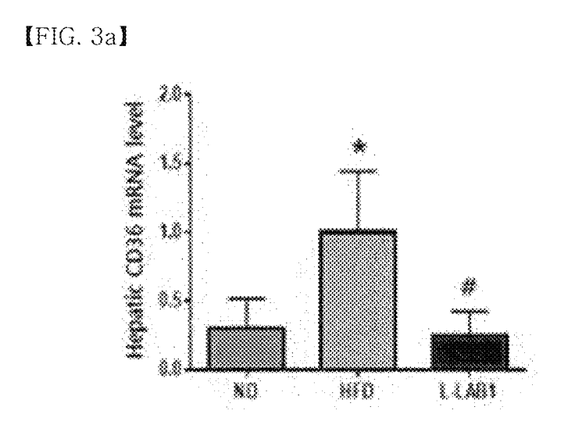
FIGS. 3a to 3c are graphs of measuring the expression level of liver tissue—related genes of the fatty liver mouse model according to the intake of the WiKim0104 strain according to the present invention. *P<0.05, compare to the ND; #P<0.05, compare to the HFD. L-LAB1 represents *Leu. citreum* WiKim0104.
Figure 3B:
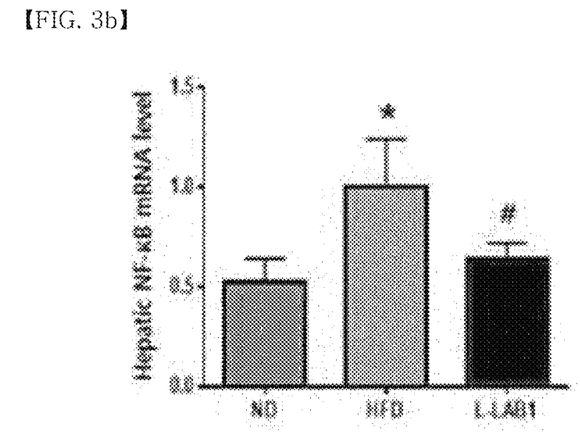
Figure 3C:
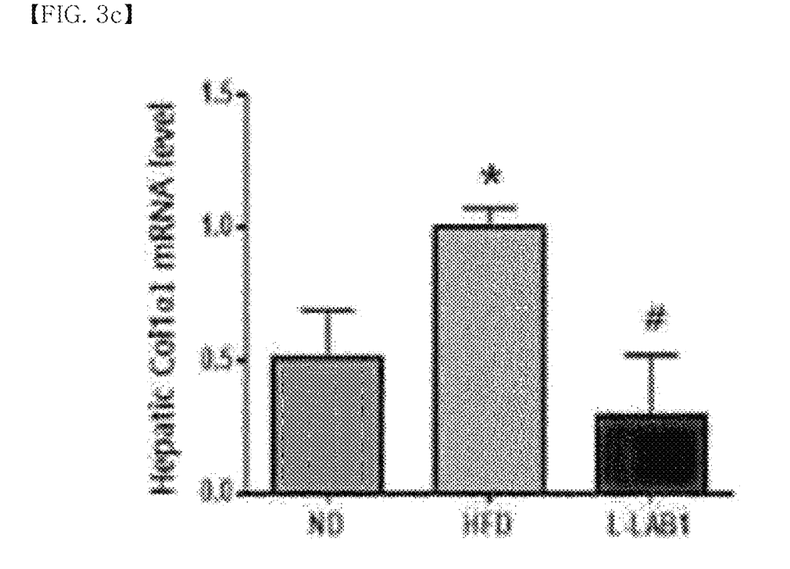
Figure 4:
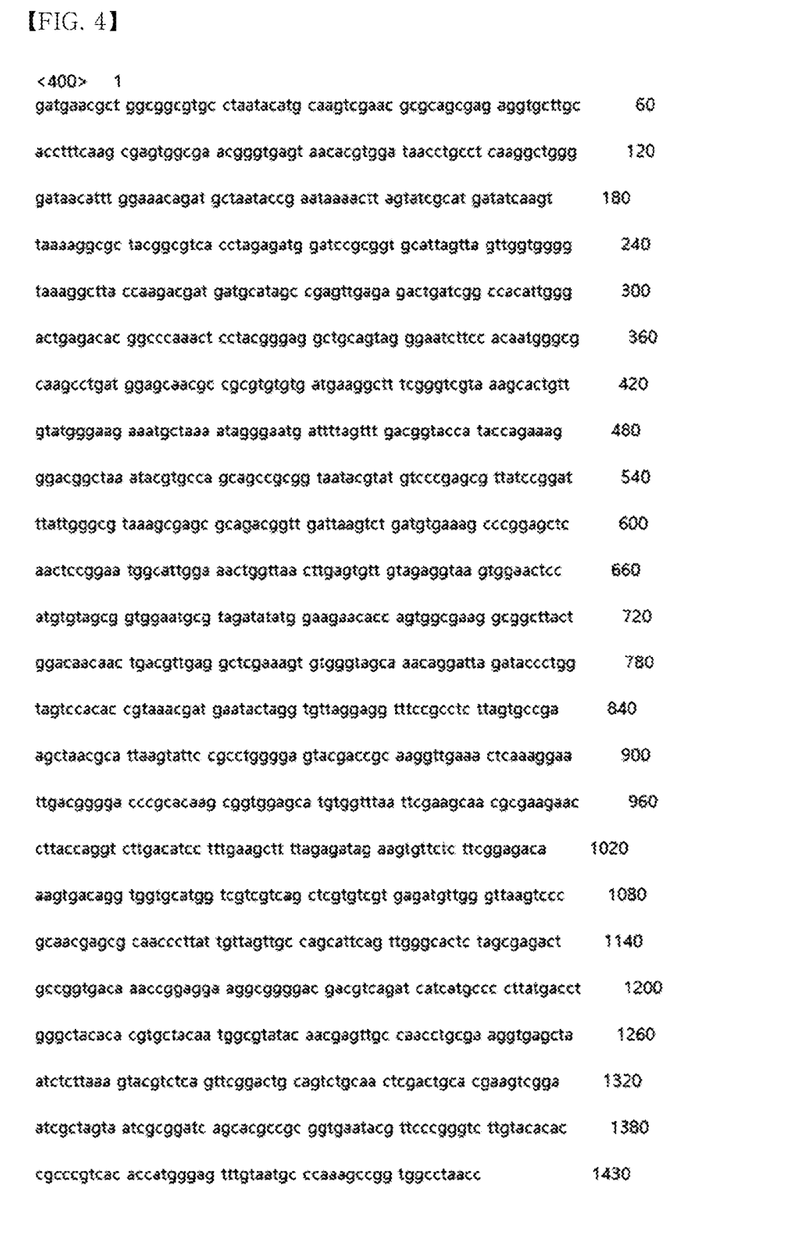
FIG. 4 shows SEQ ID NO: 1 of the present application.

As a result, as shown in FIG. 3a to FIG. 3c, it could be confirmed that the expression of genes of the fat metabolism-related factor, CD36 (Cluster of differentiation 36), inflammation-related factor, NF-κB (Nuclear factor-kappa B), and liver fibrosis-related factor, Col1α1 (Collagen type I alpha 1) was reduced, according to the intake of the *Leuconostoc citreum* WiKim0104 strain.

INDUSTRIAL AVAILABILITY

The present invention provides a novel strain. In addition, the strain of the present invention may be used as a food, feed or feed additive, pharmaceutical composition for preventing, improving or treating inflammation, obesity or fatty liver disease, or the like.

*Leuconostoc citreum* WiKim0104 has been deposited to Korean Culture Center of Microorganisms at Yurim B/D 45, Hongjenae-2ga-gil, Seodaemun-gu, Seoul 03641, Republic of Korea (international depositary authority under Budapest Treaty) under accession number KCCM12420P on Dec. 14, 2018.

[Accession Number]
  Depository authority name: Korean Culture Center of Microorganisms (Overseas)
  Accession number: KCCM12420P
  Accession date: 20181214

The invention claimed is:

1. A method of preventing, improving or treating obesity or a fatty liver disease by administering a composition comprising *Leuconostoc citreum* WiKim0104 deposited under accession number KCCM12420P, or a culture, a lysate or an extract thereof as an active ingredient to a subject in need thereof.

2. The method of claim 1, wherein the *Leuconostoc citreum* WiKim0104 deposited under accession number KCCM12420P has a 16S rDNA of SEQ ID NO: 1.

3. The method of claim 1, wherein the fatty liver disease is any one or more selected from the group consisting of simple fatty liver, non-alcoholic steatohepatitis, liver fibrosis and liver cirrhosis.

* * * * *

SEQUENCE LISTING

```
<160> NUMBER OF SEQ ID NOS: 1

<210> SEQ ID NO 1
<211> LENGTH: 1430
<212> TYPE: DNA
<213> ORGANISM: Unknown
<220> FEATURE:
<223> OTHER INFORMATION: Leuconostoc citreum WiKim0104

<400> SEQUENCE: 1
gatgaacgct ggcggcgtgc ctaatacatg caagtcgaac gcgcagcgag aggtgcttgc        60
acctttcaag cgagtggcga acgggtgagt aacacgtgga taacctgcct caaggctggg       120
gataacattt ggaaacagat gctaataccg aataaaactt agtatcgcat gatatcaagt       180
taaaaggcgc tacggcgtca cctagagatg gatccgcggt gcattagtta gttggtgggg       240
taaaggctta ccaagacgat gatgcatagc cgagttgaga gactgatcgg ccacattggg       300
actgagacac ggcccaaact cctacgggag gctgcagtag ggaatcttcc acaatgggcg       360
caagcctgat ggagcaacgc cgcgtgtgtg atgaaggctt tcgggtcgta aagcactgtt       420
gtatgggaag aaatgctaaa atagggaatg attttagttt gacggtacca taccagaaag       480
ggacggctaa atacgtgcca gcagccgcgg taatacgtat gtcccgagcg ttatccggat       540
ttattgggcg taaagcgagc gcagacggtt gattaagtct gatgtgaaag cccggagctc       600
aactccggaa tggcattgga aactggttaa cttgagtgtt gtagaggtaa gtggaactcc       660
atgtgtagcg gtggaatgcg tagatatatg gaagaacacc agtggcgaag gcggcttact       720
ggacaacaac tgacgttgag gctcgaaagt gtgggtagca aacaggatta gataccctgg       780
tagtccacac cgtaaacgat gaatactagg tgttaggagg tttccgcctc ttagtgccga       840
agctaacgca ttaagtattc cgcctgggga gtacgaccgc aaggttgaaa ctcaaaggaa       900
ttgacgggga cccgcacaag cggtggagca tgtggtttaa ttcgaagcaa cgcgaagaac       960
cttaccaggt cttgacatcc tttgaagctt ttagagatag aagtgttctc ttcggagaca      1020
aagtgacagg tggtgcatgg tcgtcgtcag ctcgtgtcgt gagatgttgg gttaagtccc      1080
```

```
gcaacgagcg caacccttat tgttagttgc cagcattcag ttgggcactc tagcgagact    1140
gccggtgaca aaccggagga aggcggggac gacgtcagat catcatgccc cttatgacct    1200
gggctacaca cgtgctacaa tggcgtatac aacgagttgc caacctgcga aggtgagcta    1260
atctcttaaa gtacgtctca gttcggactg cagtctgcaa ctcgactgca cgaagtcgga    1320
atcgctagta atcgcggatc agcacgccgc ggtgaatacg ttcccgggtc ttgtacacac    1380
cgcccgtcac accatgggag tttgtaatgc ccaaagccgg tggcctaacc              1430
```